United States Patent [19]
Hernandez et al.

[11] Patent Number: 5,094,247
[45] Date of Patent: Mar. 10, 1992

[54] BIOPSY FORCEPS WITH HANDLE HAVING A FLEXIBLE COUPLING

[75] Inventors: Ernesto Hernandez, Miami; Ernesto Avellanet, Miami Lakes, both of Fla.

[73] Assignee: Cordis Corporation, Miami, Fla.

[21] Appl. No.: 577,919

[22] Filed: Aug. 31, 1990

[51] Int. Cl.$^5$ .............................................. A61B 10/00
[52] U.S. Cl. ..................................... 128/751; 606/171
[58] Field of Search ........................ 128/749, 751, 754; 606/205-207, 171, 174

[56] References Cited

U.S. PATENT DOCUMENTS

| | | | |
|---|---|---|---|
| 3,964,468 | 6/1976 | Schulz | 606/171 X |
| 4,674,501 | 7/1987 | Greenberg | 606/174 |
| 4,763,668 | 8/1988 | Macek et al. | 128/571 |
| 4,815,476 | 3/1989 | Clossick | 128/751 |
| 4,950,273 | 8/1990 | Briggs | 606/174 X |

Primary Examiner—Max Hindenburg
Attorney, Agent, or Firm—Tarolli, Sundheim & Covell

[57] ABSTRACT

A biopsy forceps device includes a handle assembly having a handle portion and a hub portion. An elongated flexible hollow body portion preferably in the form of a coiled spring guide wire extends from the hub portion to a forceps assembly. A control wire extends through a lumen in the guide wire as well as a lumen in the hub portion and is coupled at one end to the handle portion and at the other end to the forceps assembly. A flexible coupling interconnects the hub portion with the handle portion so that the hub portion may be angularly displaced with respect to the distal end of the handle portion.

11 Claims, 1 Drawing Sheet

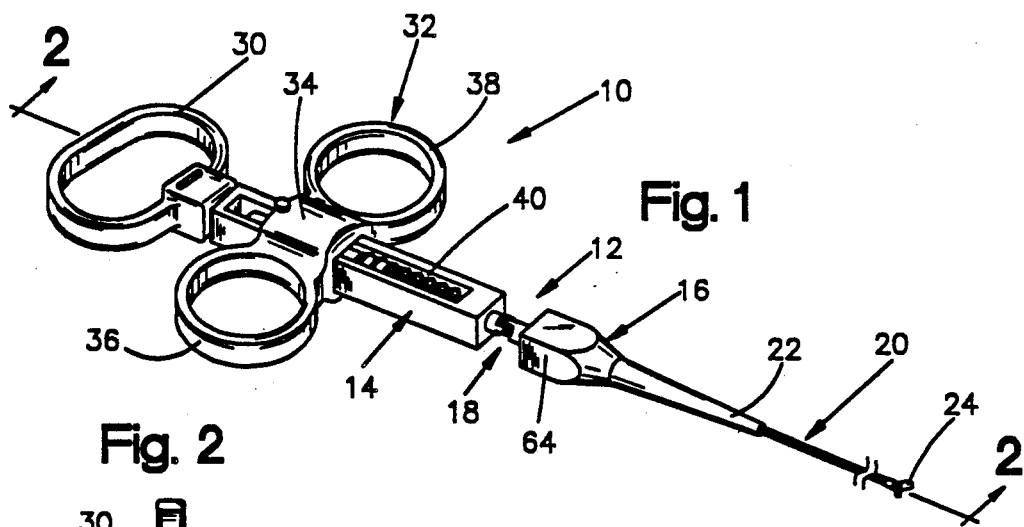
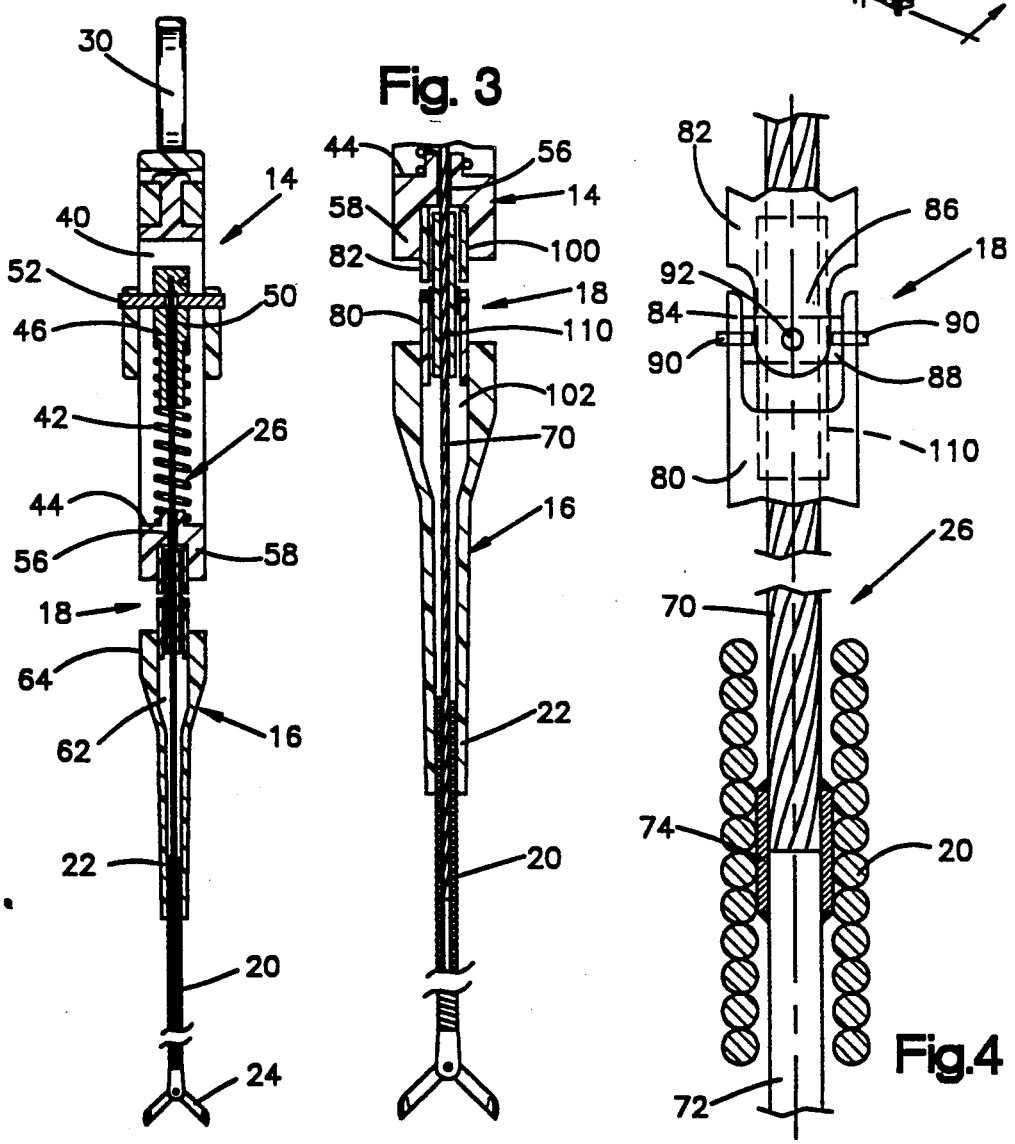

BIOPSY FORCEPS WITH HANDLE HAVING A FLEXIBLE COUPLING

RELATED APPLICATION

This application is related to our co-pending U.S. patent application Ser. No. 576,687.

FIELD OF THE INVENTION

The present invention relates to biopsy forceps and more particularly to an improved biopsy forceps having a handle assembly including a flexible coupling.

DESCRIPTION OF THE PRIOR ART

Biopsy forceps are known in the art and are in wide use for purposes of obtaining a tissue sample. One example of the prior art takes the form of the J. P. Clossick U.S. Pat. No. 4,815,476 assigned to the same assignee as the present invention. Such a forceps device includes a handle assembly slidably mounting a trigger member thereon and an elongated coil spring guide wire connected to the handle assembly at the proximal end of the guide wire. A pair of forceps are mounted to the distal end of the guide wire and a stylet-control wire received within the guide wire is connected at its proximal end to the trigger and its distal end to the pair of forceps.

A guide sheath may be introduced into a patient's body vessel, such as an artery, and the distal end of the forceps device is introduced into the sheath and guided to the site of interest. The handle assembly remains outside of the patient's body allowing the attending physician to operate the trigger. Forward movement of the trigger causes the stylet-control wire to move the forceps to an open position and rearward movement of the trigger causes the pair of forceps to move to a closed position to capture a tissue sample therebetween. The forceps device is then removed from the guide sheath so that the captured tissue may be examined. In practice, physicians have found some difficulty in operating the forceps device such as when attempting to exert sufficient force to remove the forceps device and the captured tissue from the body vessel. This could be alleviated if the handle assembly be modified such that it could pivot or rotate at an angle relative to the patient's body vessel to provide sufficient room for the physician to grasp the handle assembly and then remove the forceps from the body vessel.

SUMMARY OF THE INVENTION

In accordance with the present invention there is provided an improved biopsy forceps device having a handle assembly including a handle portion having a distal end and a hub portion connected to the distal end of the handle portion. An elongated flexible hollow body portion, such as a coil spring guide wire, is provided having a lumen extending therethrough. A forceps assembly is coupled to the distal end of the body portion with the assembly including a pair of forceps. The hub portion has a lumen extending therethrough and is coupled between the handle portion and the proximal end of the body portion. A control wire extends through the lumen in the body portion and through the lumen in the hub portion and is coupled at one end to the handle portion and the other end to the forceps assembly. A flexible coupling interconnects one end of the hub portion with the distal end of the handle portion so that the hub portion may be angularly displaced with respect to the distal end of the handle portion. This permits a physician to angularly displace the handle portion away from the patient's body when exerting force to remove the forceps and captured tissue from the patient.

In accordance with another aspect of the present invention the flexible coupling includes means for permitting angular pivotal movement between the handle portion and the hub portion in at least one plane.

In accordance with a still further aspect of the present invention the flexible coupling means includes a universal joint which permits angular pivotal movement in two mutually perpendicular planes.

DESCRIPTION OF THE DRAWINGS

The foregoing and other objects of the invention will become more readily apparent from the following description of the preferred embodiment of the invention as taken in conjunction with the accompanying drawings which are a part hereof wherein:

FIG. 1 is a perspective view of a biopsy forceps device constructed in accordance with the present invention;

FIG. 2 is a sectional view taken along line 2—2 looking in the direction of the arrows in FIG. 1;

FIG. 3 is an enlarged view of a portion of the length of that illustrated in FIG. 2; and FIG. 4 is an enlarged view of the flexible coupling shown in FIG. 3 but rotated 90 degrees.

DESCRIPTION OF THE PREFERRED EMBODIMENT

Reference is now made to the drawings wherein the drawings are for purposes of illustrating a preferred embodiment only and not for purposes of limiting same. As shown in the drawings there is provided a biopsy forceps device 10 which includes a handle assembly 12 which includes a handle portion 14 and a hub portion 16 having its proximal end connected to the distal end of the handle portion 14 by means of a flexible coupling 18, to be described in greater detail hereinafter. In addition to the handle assembly 12 the forceps device 10 includes an elongated flexible hollow body taking the form of a coil spring guide wire 20 which extends from the distal end 22 of hub portion 16 to a forceps assembly 24. The guide wire 20 has a lumen extending throughout its length and slidably receives a control wire 26 which connects at its distal end to the forceps assembly 24 and at its proximal end extends through hub portion 22, the flexible coupling 18 and then into the handle portion 14.

The handle assembly 14 includes a thumb receiving end ring 30 and a FIG. 8 shaped trigger 32. Trigger 32 has a hollow middle portion 34 slidably received over and on the handle portion 14 and opposed finger rings 36 and 38.

As best shown in FIGS. 1 and 2 the handle portion 14 has a longitudinally extending transverse slot 40 therethrough in which there is positioned a spring 42 which extends between a forward wall 44 of the slot 40 and a plug member 46 connected to the trigger 32. Connected to the plug member 46 is a proximal end 50 of the control wire 26. Specifically, the proximal end 50 of the control wire 26 is received in a bore of the plug member 46 which also has a transverse bore therein which receives a pin 52. The pin 52 extends through the middle portion 34 of the trigger 32 as well as through the plug member 46. The proximal end 50 of the wire 26 extends through a transverse passageway in the pin 52 and is anchored to the proximal end of the plug member 46. The distal end of the plug member 46 has its diameter reduced somewhat so as to receive a portion of the length of the coil spring 42 with the neck down portion of the plug member serving as a stop to hold the spring in place. The spring 42 resiliently urges the trigger member to the position as shown in FIGS. 1 and 2.

The control wire extends from the distal end of plug member 46 and then through the lumen in the coil spring 42 and then through a passageway 56 in the handle portion 14. The control wire extends through a lumen in the flexible coupling 18, to be described in greater detail hereinafter, and then through a lumen 62 in the hub portion 16.

The hub portion 16 has a proximal end 64 and an inwardly tapering conical shaped distal end 22. The control wire 26 extends through the lumen 62 of the hub member 16 and exits from the distal end of the hub member and then extends through a lumen in the coil spring guide wire 20 to the forceps assembly 24.

The proximal end of the coil spring guide wire 20 extends within the lumen 62 in the hub member 16 for a short distance and is held in place as with a press fit. The coil spring guide wire 20, containing the control wire, then extends for a length on the order of three feet to its distal end at which the control wire is connected to a pair of forceps 24.

In operation a physician employing the forceps device may insert a guide sheath into a body vessel, such as an artery, and then insert the control wire including the forceps assembly into the sheath and guide it to a site containing tissue to be captured. The forceps are opened by displacing the finger rings 36 and 38 in a forward direction against the bias of the spring 42 and then pulled rearwardly with the assistance of the spring to close the forceps to capture tissue to be removed from the patient for examination. The structure and operation of the forceps device as described herein but for the flexible coupling 18 is basically the same as that described in the aforesaid J. P. Clossick U.S. Pat. No. 4,815,476 the disclosure of which is incorporated herein.

The flexible coupling 18 facilitates the physician's use of the biopsy device since the handle portion 14 may be angularly displaced with respect to the hub portion 16 and this facilitates removing a tissue sample when employing sufficient force to the handle portion during the removal process.

In the prior art, such as in the aforesaid patent to J. P. Clossick U.S. Pat. No. 4,815,476, the control wire extending from the handle assembly to the forceps assembly is a length of solid metal. The use of such a wire extending through the flexible coupling of the present invention may well result in the wire taking on a permanent bend when the handle portion 14 is bent at a severe angle relative to the hub portion 16.

In the present invention, the control wire 26 includes a length of flexible stranded wire 70 which extends through the handle portion 14 and through the hub portion 16 and extends beyond the hub portion within the surrounding coiled spring guide wire 20. Forwardly of the distal end 22 of the hub portion the stranded wire 70 is connected to a length of solid wire 72 which then extends in a conventional manner to the distal end of the control guide wire 20 and is coupled to the forceps assembly 24. The stranded wire 70 and the solid wire 72 may be interconnected, as by welding. As shown in FIG. 4 a metal sleeve surrounds a portion of the lengths of the two wires at their abutting ends and the sleeve 74 is crimped to hold the abutting ends together and is welded or soldered to the two wires. This construction preserves the use of the solid control wire extending throughout essentially the entire length of the coil spring guide wire 20 while using a flexible strand of wire within the handle assembly and particularly through the flexible coupling so that bending thereof will not result in the flexible strand of wire taking on a permanent bend.

Attention is now directed to the flexible coupling 18 as best illustrated in FIGS. 2, 3 and 4. This flexible coupling takes the form of a universal joint. This universal joint includes a pair of tubular members 80 and 82 wherein tubular member 80 has a U-shaped yoke 84 on one end thereof which cooperates with a U-shaped yoke 86 on the abutting end of tubular member 82. A carriage member 88 interconnects the two yokes by means of pivot pins 90 and 92. That is, the pivot pins 92 connect yoke 86 with the carriage member 88 and the pivot pins 90 connect yoke 84 with the carriage member 88. The carriage member 88 has a central bore therethrough so that the control wire 26 may extend through the bore as well as through the lumen of the tubular members 80 and 82. The universal joint permits extended pivotal movement through an angle of approximately 45 degrees in two mutually perpendicular planes as well as rotational angular movement of a limited amount on the order of 15 degrees.

The universal joint interconnects the handle portion 14 with the hub portion 16. The handle portion 14 has a bore 100 in its distal end for receiving tubular member 82 which is secured thereto as by a press fit. Similarly, the proximal end of hub portion 16 has a bore 102 which receives a portion of the length of tubular member 80 and is held in place as with a press fit.

In order to keep the hub portion 16 coaxially aligned with the handle portion 14 when the forceps device is not in use or when it is not intended that there be an angular displacement therebetween, a short length of plastic tubing 110 extends through the lumen 60 of the flexible coupling and surrounds a like portion of the length of the stranded wire 70. This tubing exhibits some degree of resiliency and acts as a restoring force tending to keep the handle portion 14 and the hub portion 16 in alignment.

The outer diameter of the tubing 110 is substantially less than the inner diameter of tubular members 80 and 82 of the universal joint so as not to inhibit movement of the stranded cable 70 during operation of the trigger mechanism.

Although the invention has been described in conjunction with a preferred embodiment it is to be appreciated that various modifications may be made without departing from the spirit and scope of the invention as defined by the appended claims.

I claim as follows:

1. A biopsy forceps device comprising:
    a handle assembly including a handle portion having a distal end and a hub portion connected to the distal end of said handle portion;
    an elongated flexible hollow body portion having a lumen extending therethrough and having a proximal end and a distal end;
    a forceps assembly coupled to the distal end of said body portion, and including a pair of forceps;

said hub portion having a lumen extending therethrough, and coupled between said handle portion and the proximal end of said body portion;

control wire means extending through the lumen in said body portion and the lumen in said hub portion and coupled at one end to said handle portion and at the other end to said forceps assembly;

flexible coupling means interconnecting one end of said hub portion with the distal end of said handle portion so that said hub portion may be angularly displaced with respect to the distal end of said handle portion;

said flexible coupling means has a lumen extending therethrough with a portion of the length of said control wire means extending through the lumen in said flexible coupling means; and, said flexible coupling means is arranged to provide relative angular movement between said hub portion and said handle portion in two mutually perpendicular planes.

2. A biopsy forceps device as set forth in claim 1 wherein said control wire means includes an elongated flexible stranded wire portion and an elongated solid wire portion connected together, said stranded wire portion extending through the lumen in said flexible coupling means while said solid wire portion extends through said hollow body portion.

3. A biopsy forceps device as set forth in claim 2 wherein said stranded wire portion is more flexible than said solid wire portion permitting bending of said stranded wire portion within said flexible coupling means without resulting in a permanent bend.

4. A biopsy forceps device as set forth in claim 3 wherein one end of said stranded wire portion abuts one end of said solid wire portion and means securing said abutting ends together.

5. A biopsy forceps device as set forth in claim 1 wherein said flexible coupling means includes a universal joint.

6. A biopsy forceps device as set forth in claim 1 including an elongated tubular element of resilient material extending through the lumen in said flexible coupling means and surrounding a portion of the length of said control wire means for providing restoring forces tending to maintain alignment of the handle portion and the hub portion.

7. A biopsy forceps device comprising:

a handle assembly including a handle portion having a proximal end and a distal end and a hub portion connected to the distal end of said handle portion;

an elongated flexible hollow body portion having a lumen extending therethrough and having a proximal end and a distal end;

a forceps assembly coupled to the distal end of said body portion, and including a pair of forceps;

said hub portion having a lumen extending therethrough, and coupled between said handle portion and the proximal end of said body portion;

trigger means slidable carried by said handle portion for slidable movement between said handle portion's proximal and distal ends;

control wire means extending through the lumen in said body portion and the lumen in said hub portion and coupled at one end to said trigger means and at the other end to said forceps assembly;

flexible coupling means interconnecting one end of said hub portion with the distal end of said handle portion so that said hub portion may be angularly displaced with respect to the distal end of said handle portion;

said flexible coupling means has a lumen extending therethrough with a portion of the length of said control wire means extending through the lumen in said flexible coupling means;

said flexible coupling means is arranged to provide relative angular movement between said hub portion and said handle portion in two mutually perpendicular planes; and said ball member has a lumen extending therethrough and said control wire means extends through and beyond said ball member lumen to said trigger means.

8. A biopsy forceps device as set forth in claim 7 including an elongated tubular element of resilient material extending through the lumen in said flexible coupling means and surrounding a portion of the length of said control wire means for providing restoring forces tending to maintain alignment of the handle portion and the hub portion.

9. A biopsy forceps device as set forth in claim 8 wherein said control wire means includes an elongated flexible stranded wire portion and an elongated solid wire portion connected together, said stranded wire portion extending through the lumen in said flexible coupling means while said solid wire portion extends through said hollow body portion.

10. A biopsy forceps device as set forth in claim 9 wherein said stranded wire portion is more flexible than said solid wire portion permitting bending of said stranded wire portion within said flexible coupling means without resulting in a permanent bend.

11. A biopsy forceps device as set forth in claim 10 wherein one end of said stranded wire portion abuts one end of said solid wire portion and means securing said abutting ends together.

* * * * *